(12) United States Patent
Bijno et al.

(10) Patent No.: US 11,090,287 B2
(45) Date of Patent: Aug. 17, 2021

(54) COMPOSITION FOR THE PREVENTION AND TREATMENT OF METABOLIC DISORDERS ASSOCIATED WITH MENOPAUSE AND CLIMACTERIC

(71) Applicant: Kolinpharma S.p.A., Milan (IT)

(72) Inventors: Domenico Bijno, Milan (IT); Carmine Di Vincenzo, Milan (IT); Emanuele Lusenti, Milan (IT); Alberto Martina, Milan (IT); Ritapaola Petrelli, Milan (IT)

(73) Assignee: Kolinpharma S.p.A., Milan (IT)

( * ) Notice: Subject to any disclaimer, the term of this patent is extended or adjusted under 35 U.S.C. 154(b) by 0 days.

(21) Appl. No.: 15/503,090

(22) PCT Filed: Aug. 18, 2015

(86) PCT No.: PCT/IB2015/056272
§ 371 (c)(1),
(2) Date: Feb. 10, 2017

(87) PCT Pub. No.: WO2016/027228
PCT Pub. Date: Feb. 25, 2016

(65) Prior Publication Data
US 2017/0231954 A1    Aug. 17, 2017

(30) Foreign Application Priority Data
Aug. 20, 2014 (IT) ............... TO2014A000675

(51) Int. Cl.

| | |
|---|---|
| *A61K 31/405* | (2006.01) |
| *A23L 33/105* | (2016.01) |
| *A23L 33/175* | (2016.01) |
| *A61K 31/12* | (2006.01) |
| *A61K 31/385* | (2006.01) |
| *A23L 33/12* | (2016.01) |
| *A61K 9/00* | (2006.01) |
| *A61K 31/197* | (2006.01) |
| *A61K 31/4415* | (2006.01) |
| *A61K 33/00* | (2006.01) |
| *A61K 33/30* | (2006.01) |
| *A61K 36/9066* | (2006.01) |
| *A61K 31/375* | (2006.01) |

(52) U.S. Cl.
CPC .......... *A61K 31/405* (2013.01); *A23L 33/105* (2016.08); *A23L 33/12* (2016.08); *A23L 33/175* (2016.08); *A61K 9/0053* (2013.01); *A61K 31/12* (2013.01); *A61K 31/197* (2013.01); *A61K 31/375* (2013.01); *A61K 31/385* (2013.01); *A61K 31/4415* (2013.01); *A61K 33/00* (2013.01); *A61K 33/30* (2013.01); *A61K 36/9066* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 2004/0254122 | A1* | 12/2004 | Hayes ................ | A61K 31/405 514/23 |
| 2010/0209497 | A1* | 8/2010 | Thornthwaite ...... | A61K 31/122 424/456 |

OTHER PUBLICATIONS

Singh ("From Exotic Spice to Modern Drug?", Cell, vol. 130, 2007, pp. 765-768).*
Amin et al., "Estradiol and Tryptophan Depletion Interact to Modulate Cognition in Menopausal Women", Neuropsychopharmacology, 2006, vol. 31, pp. 2489-2497.
Bachmeier et al., "Reference Profile Correlation Reveals Estrogen-like Trancriptional Activity of Curcumin", Cellular Physiology and Biochemistry, 2010, vol. 26, pp. 471-482.
Carroll et al., "Curcumin delays development of medroxyprogesterone acetate-accelerated 7,12-dimethylbenz [α] anthracene-induced mammary tumors", Menopause, 2010, vol. 17, No. 1, pp. 178-184.
Carroll et al., "Curcumin inhibits MPA-induced secretion of VEGF from T47-D human breast cancer cells", Menopause, 2008, vol. 15, No. 3, pp. 570-574.
Cheng et al., "Reciprocal effects of α-lipoic acid on adenosine monophosphate-activated protein kinase activity in obesity induced by ovariectomy in rats", Menopause, vol. 18, No. 9, pp. 1010-1017.
Cho et al., "α-Lipoic Acid Inhibits Adipocyte Differentiation by Regulating Pro-adipogenic Transcription Factors via Mitogen-activated Protein Kinase Pathways", The Journal of Biological Chemistry, 2003, vol. 278, No. 37, pp. 34823-34833.
Fernandez-Galilea et al., "Effects of lipoic acid on lipolysis in 3T3-L1 adipocytes", Journal of Lipid Research, 2012, vol. 53, pp. 2296-2306.
Miao et al., "α-lipoic acid attenuates obesity-associated hippocampal neuroinflammation and increases the levels of brain-derived neurotrophic factor in ovariectomized rats fed a high-fat diet", International Journal of Molecular Medicine, 2013, vol. 32, pp. 1179-1186.
Miquel et al., "Menopause: A review on the role of oxygen stress and favorable effects of dietary antioxidants", Archives of Gerontology and Geriatrics, 2006, vol. 42, pp. 289-306.
Shen et al., "Lipoamide or lipoic acid stimulates mitochondrial biogenesis in 3T3-L1 adipocytes via the endothelial NO synthase-cGMP-protein kinase G signalling pathway", British Journal of Pharmacology, 2011, vol. 162, pp. 1213-1224.

(Continued)

*Primary Examiner* — David J Blanchard
*Assistant Examiner* — Sarah J Chickos
(74) *Attorney, Agent, or Firm* — MacMillan, Sobanski & Todd, LLC

(57) ABSTRACT

A pharmaceutical composition or dietary supplement with antioxidant activity, mood-regulating activity and insulin-sensitizing activity, with a consequent reduction of the accumulation of adipose tissue, is described, for use in the prevention and treatment of metabolic disorders associated with menopause and climacteric. The composition of the invention comprises, as active ingredients, a combination of alpha-lipoic acid, curcumin and L-tryptophan.

8 Claims, No Drawings

(56) References Cited

OTHER PUBLICATIONS

Teran et al., "Tryptophan Studies in Depressed Post-Menopausal Women", p. 197.
Written Opinion and International Search Report, Application No. PCT/IB2015/056272, dated Nov. 25, 2015.

* cited by examiner

COMPOSITION FOR THE PREVENTION AND TREATMENT OF METABOLIC DISORDERS ASSOCIATED WITH MENOPAUSE AND CLIMACTERIC

This is a national stage application filed under 35 U.S.C. § 371 of international application PCT/IB2015/056272, filed under the authority of the Patent Cooperation Treaty on Aug. 18, 2015, published; which claims the benefit of Patent Application No. TO2014A000675, filed on Aug. 20, 2014. The entire disclosures of all the aforementioned applications are expressly incorporated herein by reference for all purposes.

FIELD OF INVENTION

The invention relates to a composition for use as a dietary supplement or medicament in the prevention and treatment of metabolic disorders associated with menopause and climacteric.

The subject of the invention is a formulation for oral administration, which is free of particular contraindications both as regards the individuals to whom it may be administered and as regards the amounts administered, which has an antioxidant effect, a mood-regulating effect and an insulin-sensitizing effect, with a consequent reduction in the accumulation of adipose tissue.

BACKGROUND OF INVENTION

During menopause, the hypothalamo-hypophyseal axis, which directs the hormonal activities and the female cycle throughout the period of fertility, gives tension and imbalance signals: the resulting imbalance of the hormonal levels is also reflected on the production of endorphins, leading as a consequence to anxiety and mood changes. In addition, the sex hormones, in particular the oestrogens, have an influence on the levels of another neurotransmitter: serotonin. When the oestrogens decline, the serotonin levels also decrease; this is another reason why some menopausal women feel depressed. Serotonin also regulates gastrointestinal functions: sometimes, irritability, nervousness and depression are therefore accompanied by abdominal swelling, bowel irritability, difficulty in digestion, water retention and weight gain.

In menopause, with the reduction in ovarian activity, the messages sent from the cerebral control centres no longer find the appropriate response. In an attempt to re-establish equilibrium, the hypothalamus strongly activates the pituitary gland, which results in increased secretion of FSH and LH. Menopause is characterized not only by a decrease and imbalance in the hormonal levels of oestrogens and progesterone, but also by an increase in FSH and LH, which remain high even after menopause. In the transition phase, the levels of these hormones are very unpredictable, accompanied by variable symptoms, such as hot flushes, mood swings, polymenorrhoea or oligomenorrhoea.

SUMMARY OF THE INVENTION

The composition that is the subject of the present invention is characterized in that it comprises, as active ingredients, a combination of curcumin, alpha-lipoic acid and L-tryptophan.

Further characteristics of the composition of the invention and of its use are defined in the attached claims, which form an integral part of the present description.

DETAILED DESCRIPTION OF THE INVENTION

α-Lipoic acid, also known as thioctic acid or vitamin N, is produced by the body in very small amounts and may be obtained in minute amounts also from the diet in broccoli, brewer's yeast and offal.

From a chemical point of view, it is a small molecule, which is both liposoluble and water-soluble and therefore highly absorbable through the cell membrane and is capable of displaying its actions both in the aqueous phase (cytoplasmatic) and in the lipid phase (intrinsic to the cell membranes) of the cell.

The antioxidant properties of lipoic acid are due to its particular chemical structure and, mainly, to the presence of the disulfide bridge which behaves as an electron acceptor.

It exists in nature in two forms, as the cyclic disulfide (oxidized form) or as an open chain, known as dihydrolipoic acid, which bears two sulfhydryl groups; the two forms are readily interchangeable via redox reactions.

Alpha-lipoic acid acts in various ways: it has antioxidant properties, energy metabolism-modulating properties and euglycaemic properties.

As an antioxidant, it functions as a free-radical oxygen scavenger (ROS) and is capable of regenerating reduced glutathione. It participates in energy production in the mitochondria and as a catalyst of acetyl coenzyme A, involved in the ATP production process. A deficiency in alpha-lipoic acid affects the continuity of ATP energy production in the Krebs cycle.

Various studies have demonstrated that alpha-lipoic acid is capable of modulating fat metabolism. Among the mechanisms of action, mention is made of the induction of SIRT1, a particular $NAD^+$-dependent enzyme of the sirtuin family.

Alpha-lipoic acid resensitizes the insulin receptors and therefore acts as a euglycaemic agent. It increases the absorption of glucose by insulin-sensitive cells, maintaining glycaemia at a moderate level, and prevents the generation of high insulin peaks.

Curcumin, whose IUPAC name is (1E,6E)-1,7-bis(4-hydroxy-3-methoxyphenyl)hepta-1,6-diene-3,5-dione, is a compound belonging to the class of polyphenol compounds. It is obtained by solvent extraction from the dried and ground rhizome of the *Curcuma longa* plant.

Curcumin has anti-inflammatory activity, regulates glucose transport and boasts antiproliferative action on tumour cells. It reduces the synthesis of pro-inflammatory eicosanoids, via inhibition of COX2 and lipoxygenase (LOX), which are responsible for the synthesis of prostaglandins, thromboxanes and leukotrienes, which are chemical mediators of inflammatory processes.

Modification of the hormonal structure in menopausal women increases the risk of developing tumours, especially in the colon.

Curcuminoids have cellular antiproliferative activity, exerting their action on a multitude of targets via various mechanisms of action, among which are the induction of apoptosis (Nf-kb) and the inhibition of transformation of normal cells into tumour cells.

Curcumin has proven to be effective in inhibiting glucose transport into the adipocytes, blocking the translocation of the GLUT4 transport on the cell surface, and is thus capable of interfering with the mechanism of insulin resistance.

Curcumin has also shown mild phytoestrogenic activity with a mechanism based on gene regulation, which is fundamental in preventing long-term symptoms during menopause.

In the formulations according to the invention, the *Curcuma longa* extract constitutes the preferred source of curcumin. More preferably, a *Curcuma longa* extract with a curcumin titre of 95% is used. *Curcuma longa* extracts also comprise a number of curcumin derivatives, generally known as curcuminoids, among which mention may be made in particular of demethoxycurcumin and bisdemethoxycurcumin.

Tryptophan is an amino acid that is essential to the human body. Given the inability of humans to synthesize it autonomously, tryptophan must be obtained from foods; rich sources are vegetables, meat, fish, sesame seeds, chocolate and eggs.

Besides playing a key role in protein synthesis, tryptophan represents the starting point for the synthesis of various neurotransmitters, including serotonin. Serotonin is a substantially excitatory neurotransmitter, synthesized via a metabolic pathway known as tryptophan hydroxylase. Also known as the "good mood hormone", serotonin may be converted into melatonin, which is involved in regulating the sleep-wake cycle. In experimental studies aimed at evaluating the effects of tryptophan on healthy volunteers, it is observed that it is capable of increasing the perception to positive stimuli.

The combination of the above-mentioned active ingredients in the composition according to the invention is particularly advantageous since they develop a synergistic effect.

According to a preferred aspect of the present invention, the compositions under consideration may contain additional components, with curative or complementary action, or else may be useful for the purposes of the proposed invention. Examples of such additional components are chromium (preferably in the form of chromium picolinate), vitamin C, zinc (preferably in the form of zinc bisglycinate), vitamin B5 and vitamin B6.

Chromium is an oligoelement present in trace amounts in the human body. Chromium contributes towards maintaining normal levels of glucose in the blood and studies demonstrate that the improvement in homeostasis in the blood is achieved in particular by the enzyme AMPK. The activity of this enzyme is increased when the cellular levels of ATP decrease.

The important role of chromium as a cofactor in potentiating insulin function has been known for a long time. Chronic deficiency in chromium reduces the body's sensitivity to insulin, increases cholesterol and lowers the immune defences.

Vitamin C is a water-soluble vitamin which is a cofactor of important reactions in collagen maturation, such as the hydroxylation of lysine and proline by proline hydroxylase and lysine hydroxylase Vitamin C contributes towards collagen formation for the normal function of cartilage.

Zinc bisglycinate chelate aids in maintaining normal levels of testosterone in the blood. The sex hormones are transported into the blood by a globulin, SHBG, which also binds a Zn ion. The binding of sex steroids and their transportation to the target organs depend on the concentration of zinc in the blood.

Further ingredients that are useful in the composition that is the subject of the present invention are vitamin B5, which aids in reducing tiredness and fatigue, and vitamin B6, which contributes towards regulating hormonal activity.

The compositions of the invention may be formulated in any form suitable for oral administration, for instance soft or hard gelatin capsules, tablets, effervescent or chewable tablets, granules or powders in a sachet, controlled-release solid forms, chewing gums and the like.

The compositions of the present invention may be formulated in a manner suitable for oral administration and will be prepared according to conventional methods that are well known in the pharmaceutical field, such as those described in "Remington's Pharmaceutical Handbook", Mack Publishing Co., N.Y., USA, using excipients, diluents, fillers and anticaking agents that are acceptable for the final use thereof.

A particularly preferred formulation of the composition of the invention is reported hereinbelow. Besides the active ingredients indicated, the formulation may also comprise pharmaceutically acceptable excipients, vehicles and/or diluents.

Formulation Example—1.25 g Tablets

| INGREDIENTS | mg/tablet |
|---|---|
| Dry extract of *Curcuma* (*Curcuma longa*, root) 95% titre of curcumin (24%) | 300.00 |
| Lipoic acid | 300.00 |
| L-Tryptophan | 150.00 |
| Vitamin C | 125.00 |
| Zinc bisglycinate | 15.63 |
| Pantothenic acid Vitamin B5 | 9.76 |
| Pyridoxine hydrochloride Vitamin B6 | 2.886 |
| Chromium picolinate | 0.4167 |

The recommended dose is one or two tablets per day.

Experimental Section

α-Lipoic acid (LA) is a natural compound with effects on the metabolism of adipocytes, which are cells devoted to synthesizing, accumulating and yielding fats. In particular, its effect on 3T3-L1 cells has been studied and it is reported in the literature that LA has dose- and time-dependent lipolytic action (Fernandez-Galilea et al., 2012, Journal of Lipid Research) and stimulates the activity of the mitochondria (Shen et al., 2011, British Journal of Pharmacology), the cellular organelle being involved in producing energy in the form of ATP, in mature adipocytes. In addition, LA inhibits the differentiation of preadipocytes into mature adipocytes (Cho et al., 2003, The Journal of Biological Chemistry).

An experimental study was performed for the purpose of evaluating the effect of the composition of the above formulation example, referred to hereinbelow as Almetax, in the context of LA, for revealing possible synergism between the components of the mixture.

In particular, the following analyses were performed:

1. Preliminary evaluation of the cytotoxicity of the compound and identification of the treatment dose and treatment times.

2. Quantification of ATP production after treatment to evaluate the activation of cell metabolism.

3. Quantification of lipolysis. Quantification of the cytoplasmatic accumulation of fats for evaluation of the reabsorption after treatment.

4. Quantification of the oxygen free radicals (ROS) produced after treatment for evaluation of the antioxidant effect.

5. Evaluation of cell proliferation after treatment to evaluate the de-differentiation.

The invention claimed is:

1. A pharmaceutical composition or dietary supplement comprising a combination of active ingredients present in a therapeutically effective amount:
   i) *Curcuma longa* extract obtained by solvent extraction from dried and powdered rhizome of the *Curcuma longa* plant,
   ii) alpha-lipoic acid obtained from a source other than the *Curcuma longa* plant, and
   iii) L-tryptophan obtained from a source other than the *Curcuma longa* plant,
   wherein the alpha-lipoic acid present in the pharmaceutical act to bind to the *Curcuma longa* extract and L-tryptophan to aid in absorption of the pharmaceutical composition through cell membrane;
   the active ingredients being combined and formulated into the pharmaceutical composition for use in the treatment and prevention of pathologies associated with climacteric and menopause in a mammal, said pathologies being selected from the group consisting of glucose-lipid dysmetabolism, body weight modification, general tissue ageing, and combinations thereof, or in the prevention of tumours,
   wherein the active ingredients are present in the pharmaceutical composition in a tablet or capsule dosage form of about: 250 to 400 mg of alpha-lipoic acid, 200 to 400 mg of *Curcuma longa* extract, and 100 to 200 mg of L-tryptophan.

2. The pharmaceutical composition or dietary supplement according to claim 1, wherein said *Curcuma longa* extract has a curcumin titre of about 95%.

3. The pharmaceutical composition or dietary supplement according to claim 1, wherein the active ingredients are present in the pharmaceutical composition in a tablet or capsule dosage form of: about 300 mg of alpha-lipoic acid, about 300 mg of *Curcuma longa* extract, and about 150 mg of L-tryptophan.

4. The pharmaceutical composition or dietary supplement according to claim 1, which is in an oral dosage form.

5. The pharmaceutical composition or dietary supplement according to claim 1, formulated for use in oral administration, wherein the active ingredients in the pharmaceutical composition are present in amounts ranging: from 250 to 800 mg/day of alpha-lipoic acid, from 200 to 800 mg/day of *Curcuma longa* extract, and from 100 to 400 mg/day of L-tryptophan.

6. A pharmaceutical composition or dietary supplement comprising a combination of active ingredients present in a therapeutically effective amount:
   i) *Curcuma longa* extract obtained by solvent extraction from dried and powdered rhizome of the *Curcuma longa* plant,
   ii) alpha-lipoic acid obtained from a source other than the *Curcuma longa* plant, and
   iii) L-tryptophan obtained from a source other than the *Curcuma longa* plant,
   the ingredients being combined and formulated into the pharmaceutical composition, and
   the pharmaceutical composition further includes one or more further active ingredient selected from vitamin C, zinc, zinc bisglycinate, chromium, chromium picolinate, vitamin B5 and vitamin B6.

7. The composition according to claim 1, further comprising pharmaceutically acceptable excipients and/or binders and/or vehicles.

8. A pharmaceutical composition or dietary supplement comprising a combination of active ingredients (mg/tablet) formulated for oral administration as a tablet or capsule, and present in therapeutically effective amounts of:
   dry extract of Curcuma (*Curcuma longa*, root) 95% titre of curcumin (24%) 300.00
   lipoic acid 300.00
   L-Tryptophan 150.00
   vitamin C 125.00
   zinc bisglycinate 15.63
   pantothenic acid Vitamin B5 9.76
   pyridoxine hydrochloride Vitamin B6 2.886, and
   chromium picolinate 0.4167.

* * * * *